(12) United States Patent
Odate

(10) Patent No.: US 12,285,057 B2
(45) Date of Patent: Apr. 29, 2025

(54) PANTS WITH BELT

(71) Applicant: Susumu Odate, Kanagawa (JP)

(72) Inventor: Susumu Odate, Kanagawa (JP)

(*) Notice: Subject to any disclaimer, the term of this patent is extended or adjusted under 35 U.S.C. 154(b) by 0 days.

(21) Appl. No.: 17/908,878

(22) PCT Filed: Mar. 1, 2021

(86) PCT No.: PCT/JP2021/007672
§ 371 (c)(1),
(2) Date: Sep. 1, 2022

(87) PCT Pub. No.: WO2021/177221
PCT Pub. Date: Sep. 10, 2021

(65) Prior Publication Data
US 2024/0292909 A1    Sep. 5, 2024

(30) Foreign Application Priority Data
Mar. 3, 2020 (JP) ................. 2020-036033

(51) Int. Cl.
*A41C 1/10* (2006.01)

(52) U.S. Cl.
CPC .................... *A41C 1/10* (2013.01)

(58) Field of Classification Search
CPC ...................................... A41C 3/10
USPC ......................................... 450/155
See application file for complete search history.

(56) References Cited

U.S. PATENT DOCUMENTS

| | | | | |
|---|---|---|---|---|
| 4,557,268 A | * | 12/1985 | Maddux | A41C 1/10 450/155 |
| 4,697,592 A | * | 10/1987 | Maddux | A41C 1/10 450/155 |
| 6,620,026 B1 | * | 9/2003 | Guilani | A41C 1/10 450/96 |
| 2017/0143047 A1 | * | 5/2017 | Howard | A41D 13/0525 |
| 2019/0125593 A1 | * | 5/2019 | Xiong | A61F 13/496 |
| 2024/0292909 A1 | * | 9/2024 | Odate | A41F 9/02 |

FOREIGN PATENT DOCUMENTS

| | | |
|---|---|---|
| JP | 6025234 Y2 | 7/1985 |
| JP | 200652475 A | 2/2006 |
| JP | 201660978 A | 4/2016 |
| JP | 2016223052 A | 12/2016 |

* cited by examiner

*Primary Examiner* — Gloria M Hale
(74) *Attorney, Agent, or Firm* — Muncy, Geissler, Olds & Lowe, P.C.

(57) ABSTRACT

A pair of belt-attached pants includes a pants main body having a waistband part and a waist part configured to cover a lower abdomen above a pubis of a wearer and below the waistband part, a first belt having a first fixed part that is fixed to a back surface of the waist part, a second belt having a second fixed part that is fixed to the front surface of the waist part, a fastening part that makes the second belt fastenable to the first belt, wherein the first belt and the second belt are formed of a member having stretchability lower than stretchability of the waist part, and the second belt is configured to support the lower abdomen above the pubis of the wearer upward by fastening the first belt to the second belt through the fastening part.

5 Claims, 12 Drawing Sheets

PANTS WITH BELT

CROSS-REFERENCE TO RELATED APPLICATIONS

This is a 35 U.S.C. 371 National Stage Patent Application of International Application No. PCT/JP2021/007672, filed Mar. 1, 2021, which claims priority to Japanese application 2020036033, filed Mar. 3, 2020 which is hereby incorporated by reference in its entirety.

TECHNICAL FIELD

The present invention relates to a pair of belt-attached pants in which a belt and a pair of pants are integrated.

BACKGROUND ART

Conventionally, as a pair of belt-attached pants having a belt that restrains a lower abdomen, for example, an obstetrical binder described in Patent Literature 1 and a maternity support described in Nonpatent Literature 1 are disclosed.

These are both provided with a belt having a length in which a central part in a longitudinal direction is fixed to a crotch portion of a pair of pants (including a girdle or the like) for a pregnant woman and both end parts reach the positions of both sides of a part covering the upper part of the pants from the pelvis, and the degree of tightening is adjustable by fastening positions of the both end parts of the belt. That is, an object of the present invention is to support the abdomen of a pregnant woman that gradually grows while adjusting the degree of tightening according to the size at that time. In addition, in the maternal support of Nonpatent Literature 2, both end parts of the belt are peeled off from a fastening part formed of a hook-and-loop fastener, and thus the maternal support can be easily attached and detached similarly to pairs of normal pants. In addition, since the peeled belt portion hangs forward, the belt portion can be visually observed at the time of attachment and detachment.

CITATION LIST

Patent Literature

Patent Literature 1: JP-UM-A-57-57827

Nonpatent Literature

Nonpatent Literature 1: [Searched on Jan. 23, 2020], Internet (URL: https://www.rosemadane.co.jp/fs/mamaplus/102-6050-01)

SUMMARY OF THE INVENTION

Problems to be Solved by the Invention

However, since the pairs of belt-attached pants of Patent Literature 1 and Nonpatent Literature 1 are intended for a pregnant woman, as illustrated in FIG. 12, rather than tightening the lower abdomen, the lower abdomen bulging due to pregnancy is supported so as to be lifted upward from the lower position of a pubis 40 like a hammock. Besides, in the pairs of belt-attached pants of Patent Literature 1 and Nonpatent Literature 1, in order to easily lift the lower abdomen from the lower side, as illustrated in FIG. 12, only the lower end part of the central part of the belt portion is fixed at a fixed position 200f in FIG. 12, and the entire belt portion can be tilted forward (see FIG. 2 of Patent Literature 1). As described above, since the pairs of belt-attached pants of Patent Literature 1 and Nonpatent Literature 1 support the lower abdomen of the pregnant woman, the pairs of belt-attached pants are not suitable for the use of tightening the lower abdomen above the pubis to prevent the abdominal wall from expanding or for the use of fixing the waist.

Therefore, unlike such a conventional technique, an object of the present invention is to provide a pair of belt-attached pants suitable for fastening a lower abdomen above a pubis around the waist to prevent the abdominal wall from expanding and for fixing the waist.

Solution to the Problems

[Invention 1]

In order to achieve the above object, a pair of belt-attached pants of invention 1 includes: a pants main body having a waist part that is a tubular part covering a lower abdomen above a pubis of a human body around a waist when worn, at least the waist part being formed to have stretchability; the first belt having a part fixed to a back surface side of the waist part, and having two first other parts sandwiching the part, the first other parts going around from the back surface side to a front surface side along the waist part, the first other parts being fixed to the front surface side of the waist part at a predetermined interval; a second belt having a part fixed to the front surface side of the waist part, the second belt having two second other parts sandwiching the part, the second belt having a length in which the two second other parts reach at least both side parts of the waist part respectively to sides away from the part on the front surface side along the waist part; and a fastening part that makes one of the second other parts fastenable to one of the first other parts and makes the other of the second other parts fastenable to the other of the first other parts.

With such a configuration, after the pair of belt-attached pants is worn, the second other parts of the second belt on the front surface side of the pants main body and on the front surface side of the waist part can be pulled respectively to sides away from a part of the front side along the waist part. Subsequently, the second other parts can be respectively fastened to the first other parts on the corresponding sides of the first belt at the positions of both sides of the pants main body by the fastening parts. As a result, the lower abdomen above the pubis is tightened around the waist by the first belt and the second belt.

[Invention 2]

Furthermore, in the pair of belt-attached pants of invention 1, in a pair of belt-attached pants of invention 2, the first belt has a central part in a longitudinal direction fixed to a central part of the waist part on the back surface side of the pants main body, and the second belt has a central part in the longitudinal direction fixed to a central part of the waist part on the front surface side.

With such a configuration, the first other parts of the first belt are formed to have equal lengths, and the second other parts of the second belt are formed to have equal lengths. Besides, the central part in the longitudinal direction of the second belt is fixed to a part of the waist part covering the central part of the lower abdomen above the pubis when worn.

[Invention 3]

Furthermore, in the pair of belt-attached pants of invention 1 or invention 2, in a pair of belt-attached pants of invention 3, the first and second belts are formed of a member having stretchability lower than stretchability of the waist part.

With such a configuration, the lower abdomen above the pubis is tightened around the waist by the first belt and the second belt formed of a member having stretchability lower than that of the waist part.

[Invention 4]

Furthermore, in the pair of belt-attached pants of any one of invention 1 to invention 3, in a pair of belt-attached pants of invention 4, the fastening part is formed such that the second other parts are fastenable to a given position along the longitudinal direction of corresponding one or the other of the first other parts of the first belt.

With such a configuration, it is possible to adjust the fastening positions of the second other parts of the second belt respectively at given positions along the longitudinal direction of the corresponding first other parts of the first belt.

[Invention 5]

Furthermore, in the pair of belt-attached pants of any one of invention 1 to invention 4, in a pair of belt-attached pants of invention 5, in the first belt, a part other than parts of the first other parts on tip end sides is non-fixed, and the non-fixed part is formed to have a dimension longer than a length of a part of the waist part in a non-stretched state to which the non-fixed part is faced.

With such a configuration, it is possible to extend and widen the waist part by the dimension of the difference from the part, facing the waist part, of the non-fixed part.

[Invention 6]

In order to achieve the object, a pair of belt-attached pants of invention 6 includes: a pants main body having a waist part that is a tubular part covering a lower abdomen above a pubis of a human body around a waist when worn, the waist part being formed such that a part on a front surface side has stretchability than higher than stretchability of another part; a belt having a part fixed to the front surface side of the waist part, the belt having two other parts sandwiching the part, the belt having a length in which the two other parts reach at least both side parts of the waist part respectively to sides away from the part on the front surface side along the waist part; and a fastening part that makes one of the other parts of the belt fastenable to one of the both side parts of the waist part, and makes the other of the other parts fastenable to the other of the both side parts.

With such a configuration, after the pair of belt-attached pants is worn, the other parts of the belt on the front surface side of the pants main body and on the front surface side of the waist part can be pulled along the waist part respectively to sides away from the part on the front surface side. Subsequently, one and the other of these other parts can be respectively fastened to the corresponding sides of the both side parts of the pants main body. As a result, the lower abdomen above the pubis is tightened around the waist by the belt and the part, having low stretchability, of the waist part.

Effects of the Invention

As described above, according to the pair of belt-attached pants of invention 1, it is possible to suppress the expansion of the abdominal wall with respect to the lower abdomen above the pubis and to fix the waist. As a result, for example, it is possible to suppress the bulging of the lower abdomen (sticking out abdomen) due to the opening of the pelvis and the looseness of the lower abdomen after delivery. Besides, it is possible to suppress the bulging of the lower abdomen (sticking out abdomen) due to the looseness of pelvic floor muscles and abdominal wall muscles (in the following, referred to as "abdominal wall muscle") regardless of the gender, and it is possible to effectively perform an exercise for eliminating the looseness of the abdominal wall muscles. Furthermore, since the first and second belts are fixed to the pants main body, it is possible to make the belt less likely to be displaced from the point where the lower abdomen is pressed. Furthermore, since the belt can be prevented from interfering with the part, covering the lower side from the pubis, of the pants main body, it is possible to easily provide the front opening, the chuck, and the like for men.

In addition, according to the pair of belt-attached pants of invention 2, when the pair of belt-attached pants is worn, the central part of the second belt can be positioned at the central part of the lower abdomen, and the two other parts sandwiching the central part are formed to have an equal length. Thus, by pulling the two other parts toward the back surface side with the central part of the lower abdomen as the center and fastening the two other parts of the second belt to the two other parts of the first belt, it is possible to easily tighten the lower abdomen in a well-balanced manner.

In addition, according to the pair of belt-attached pants of invention 3, it is possible to tighten the lower abdomen above the pubis more firmly around the waist by the first and second belts. As a result, it is possible to make the first and second belts less likely to deviate from the pressing point. Besides, it is possible to more firmly suppress the expansion of the abdominal wall and to increase the abdominal pressure. As a result, it is possible to further enhance the effect of muscle strength training such as abdominal muscles, and it is possible to stabilize the trunk to reduce the burden on the body such as the waist during exercise, housework, and work.

In addition, according to the pair of belt-attached pants of invention 4, since the force of tightening the lower abdomen around the waist can be adjusted in a stepwise manner by adjusting the fastening position, for example, it is possible to easily tighten the lower abdomen around the waist with the best tightening force suitable for the user.

In addition, according to the pair of belt-attached pants of invention 5, it is possible to easily wear and take off the pair of belt-attached pants.

In addition, according to the pair of belt-attached pants of invention 6, it is possible to obtain the same effect as the effect of invention 1 above.

BRIEF DESCRIPTION OF THE DRAWINGS

FIG. 1 illustrates a state in which the pair of belt-attached pants 1 not worn is placed flat and illustrates a state in which both of second belt pieces 120 and 121 of a second belt 12 are not fastened to a first belt 11.

FIG. 2 illustrates a state in which the pair of belt-attached pants 1 not worn is placed flat, and illustrates a state in which the second belt piece 120 of the second belt 12 is fastened to a first belt piece 110 of the first belt 11.

FIG. 3 illustrates a state in which the pair of belt-attached pants 1 not worn is placed flat, and illustrates a state in which either of the second belt pieces 120 and 121 of the second belt 12 are not fastened to the first belt 11.

FIG. 4 illustrates a state in which the pair of belt-attached pants 1 not worn is placed flat, and illustrates a state in which the second belt pieces 120 and 121 of the second belt 12 are both shallowly fastened to the first belt piece 110 and a first belt piece 111 of the first belt 11.

FIG. 5 illustrates a state in which the pair of belt-attached pants 1 not worn is placed flat, and illustrates a state in which the second belt pieces 120 and 121 of the second belt 12 are both deeply fastened to the first belt pieces 110 and 111 of the first belt 11.

FIG. 6 illustrates a state in which either of the second belt pieces 120 and 121 of the second belt 12 are not fastened to the first belt 11.

FIG. 7 illustrates a state in which the second belt piece 121 of the second belt 12 is fastened to the first belt piece 111 of the first belt 11.

FIG. 8 illustrates a state in which either of the second belt pieces 120 and 121 of the second belt 12 are not fastened to the first belt 11.

FIG. 9 illustrates a state in which either of the second belt pieces 120 and 121 of the second belt 12 are not fastened to the first belt 11.

FIG. 10 illustrates a state in which the second belt pieces 120 and 121 of the second belt 12 are both fastened to the first belt pieces 110 and 111 of the first belt 11.

In FIG. 11, the tightening position of the pair of belt-attached pants 1 according to the present embodiment is indicated by a broken line, and the direction of the tightening force of the pair of belt-attached pants 1 is indicated by an arrow.

In FIG. 12, the tightening position of a pair of belt-attached pants 200 of the conventional art is indicated by a broken line, and the direction of the tightening force of the pair of belt-attached pants 200 is indicated by an arrow.

FIG. 13 illustrates a state in which either of the second belt pieces 120 and 121 of the second belt 12 are not fastened to the first belt 11A.

DESCRIPTION OF THE EMBODIMENTS

[Configuration]

In the following, an embodiment of the present invention will be described. FIGS. 1 to 11 are views illustrating the present embodiment. Note that the drawings are schematic. Therefore, it should be noted that the relationship between thicknesses and the plane dimensions, ratios, and the like may be different from the actual ones, and in some cases, parts having the relationships or ratios different from each other also between the drawings are included. In addition, the embodiment shown below exemplifies an article that embodies the technical idea of the present invention, and the technical idea of the present invention does not specify the material, shape, structure, arrangement, and the like of the component in the embodiment below.

First, a configuration of the present embodiment will be described.

Figure 1:
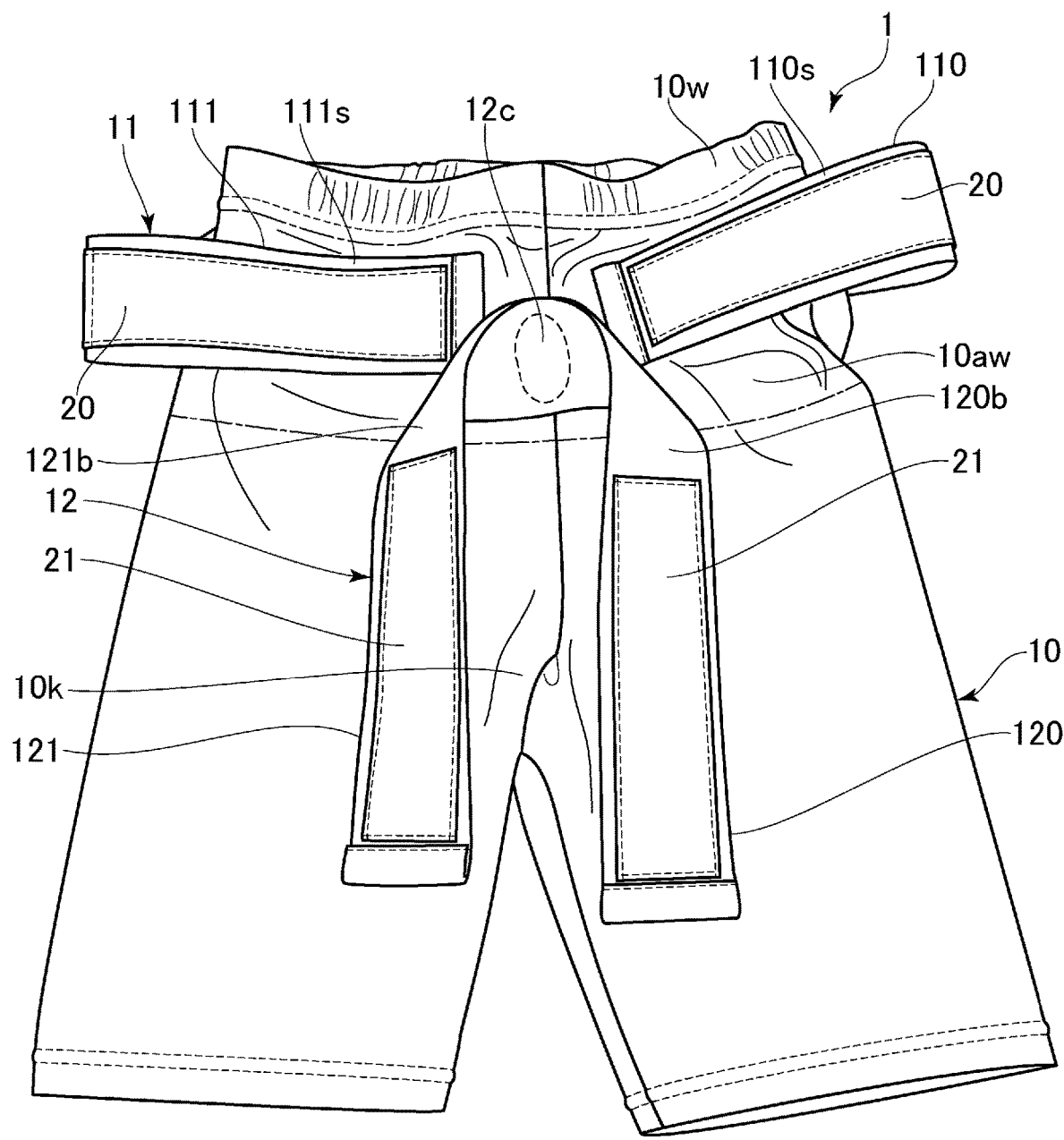
FIG. 1 is a front view of a pair of belt-attached pants 1 according to the present embodiment.
Figure 2:
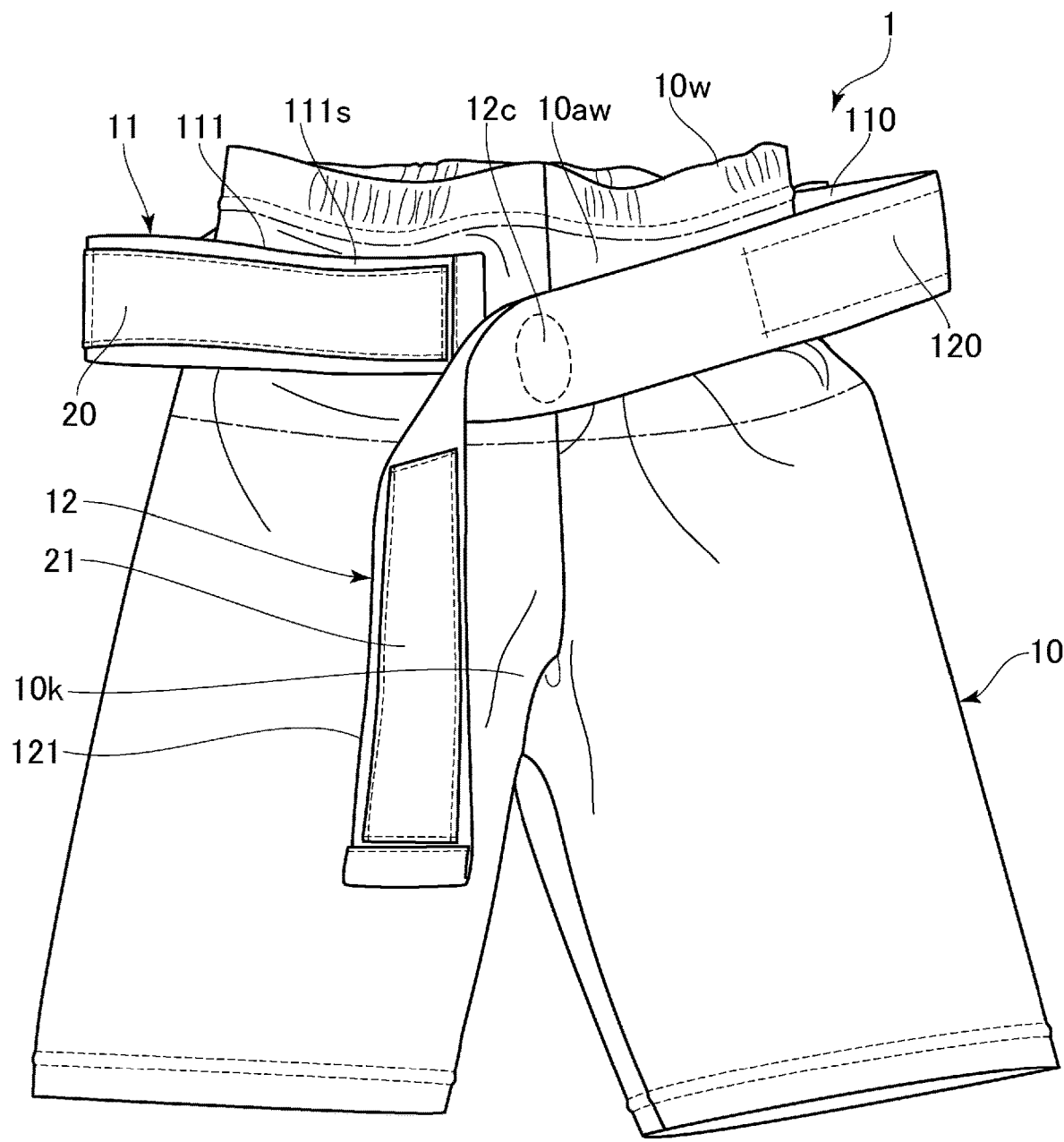
FIG. 2 is a front view of the pair of belt-attached pants 1 according to the present embodiment.
Figure 3:
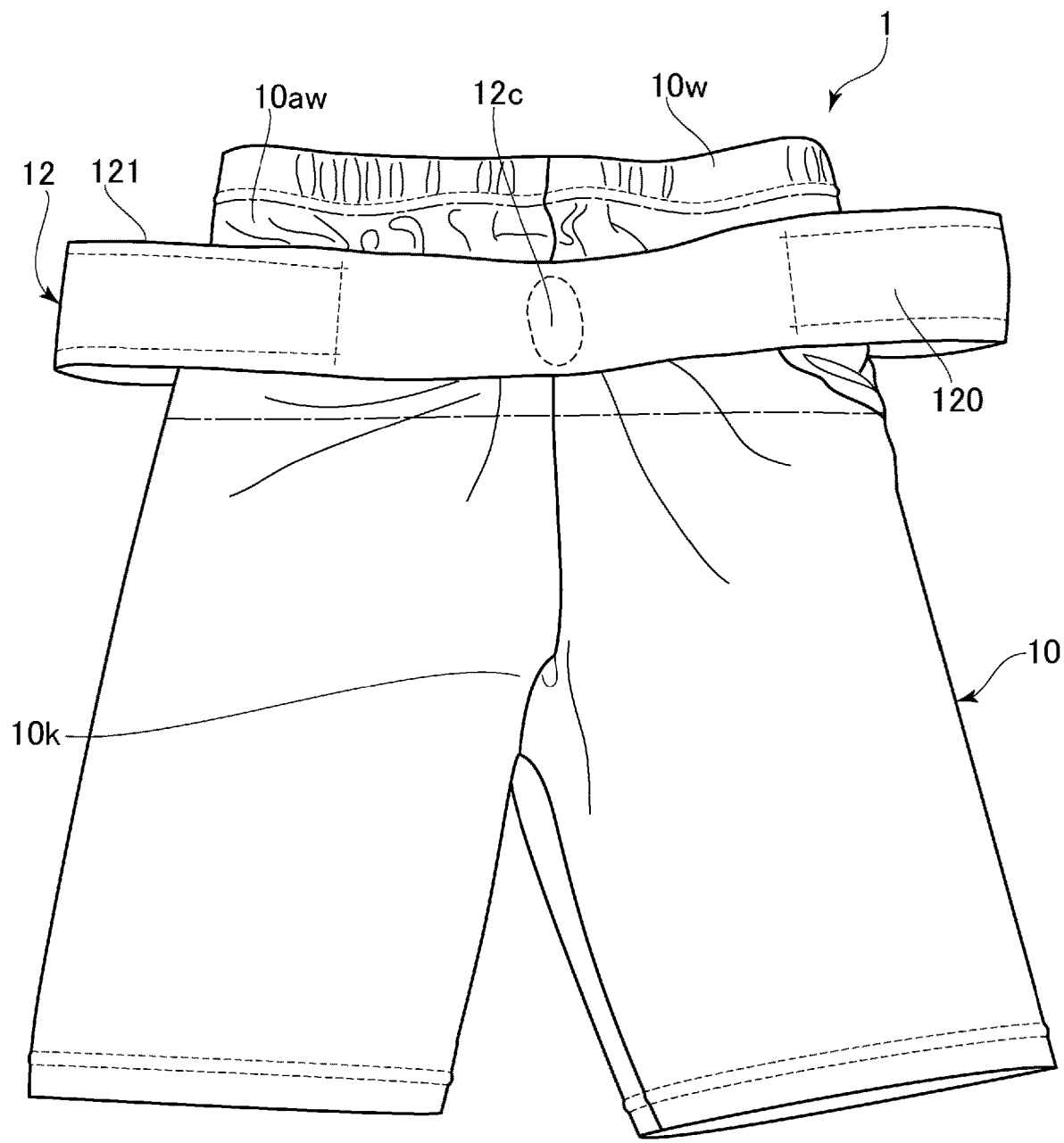
FIG. 3 is a front view of the pair of belt-attached pants 1 according to the present embodiment.

FIGS. 1 to 3 are front views of a pair of belt-attached pants 1 according to the present embodiment. FIG. 1 illustrates a state in which second belt pieces 120 and 121 of a second belt 12 are not fastened to a first belt 11. In addition, FIG. 2 illustrates a state in which the second belt piece 120 is fastened to a first belt piece 110 of the first belt 11. In addition, FIG. 3 illustrates a state in which the second belt pieces 120 and 121 are fastened to the first belt piece 110 and a first belt piece 111 of the first belt 11.

Figure 4:
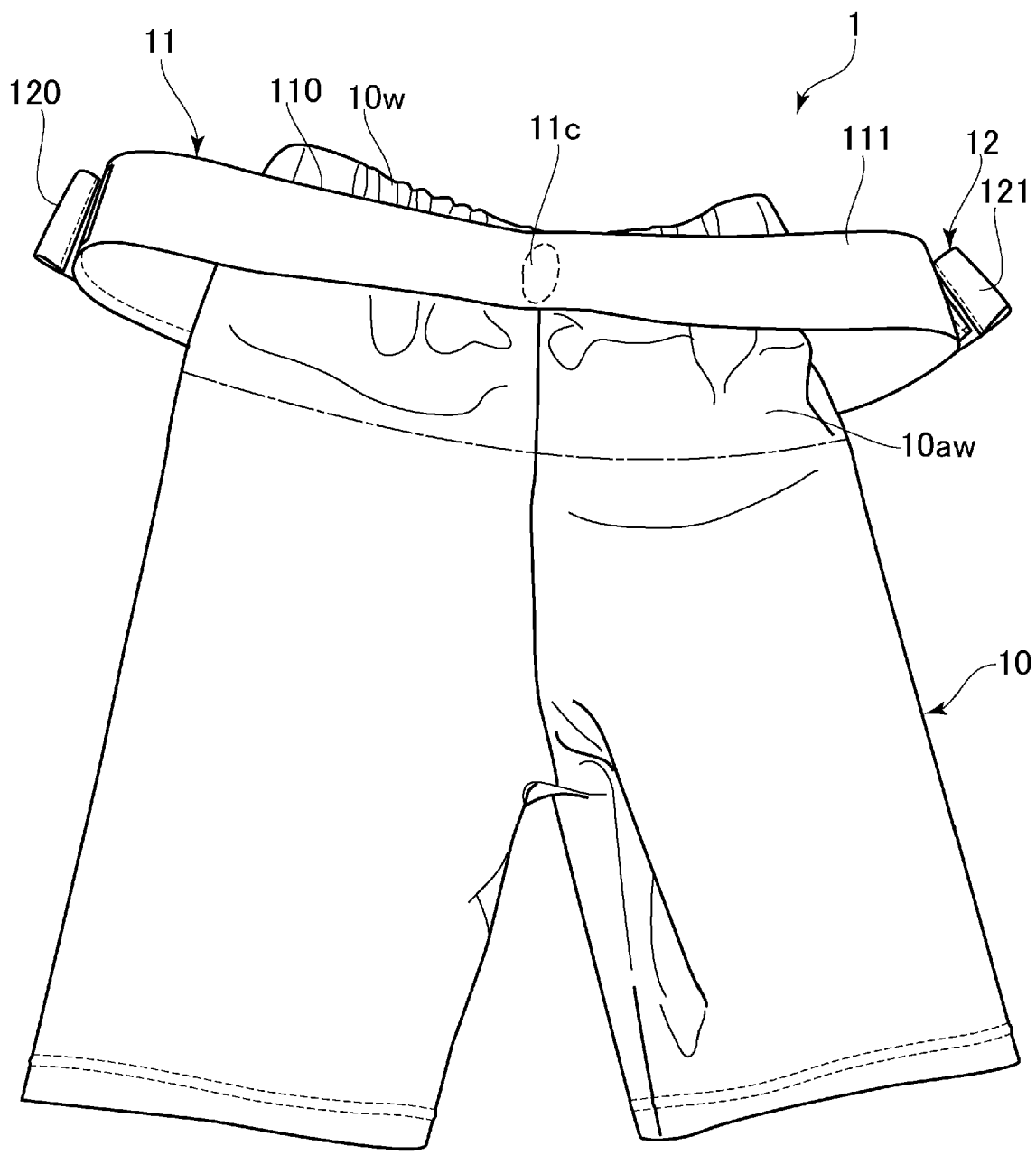
FIG. 4 is a rear view of the pair of belt-attached pants 1 according to the present embodiment.
Figure 5:
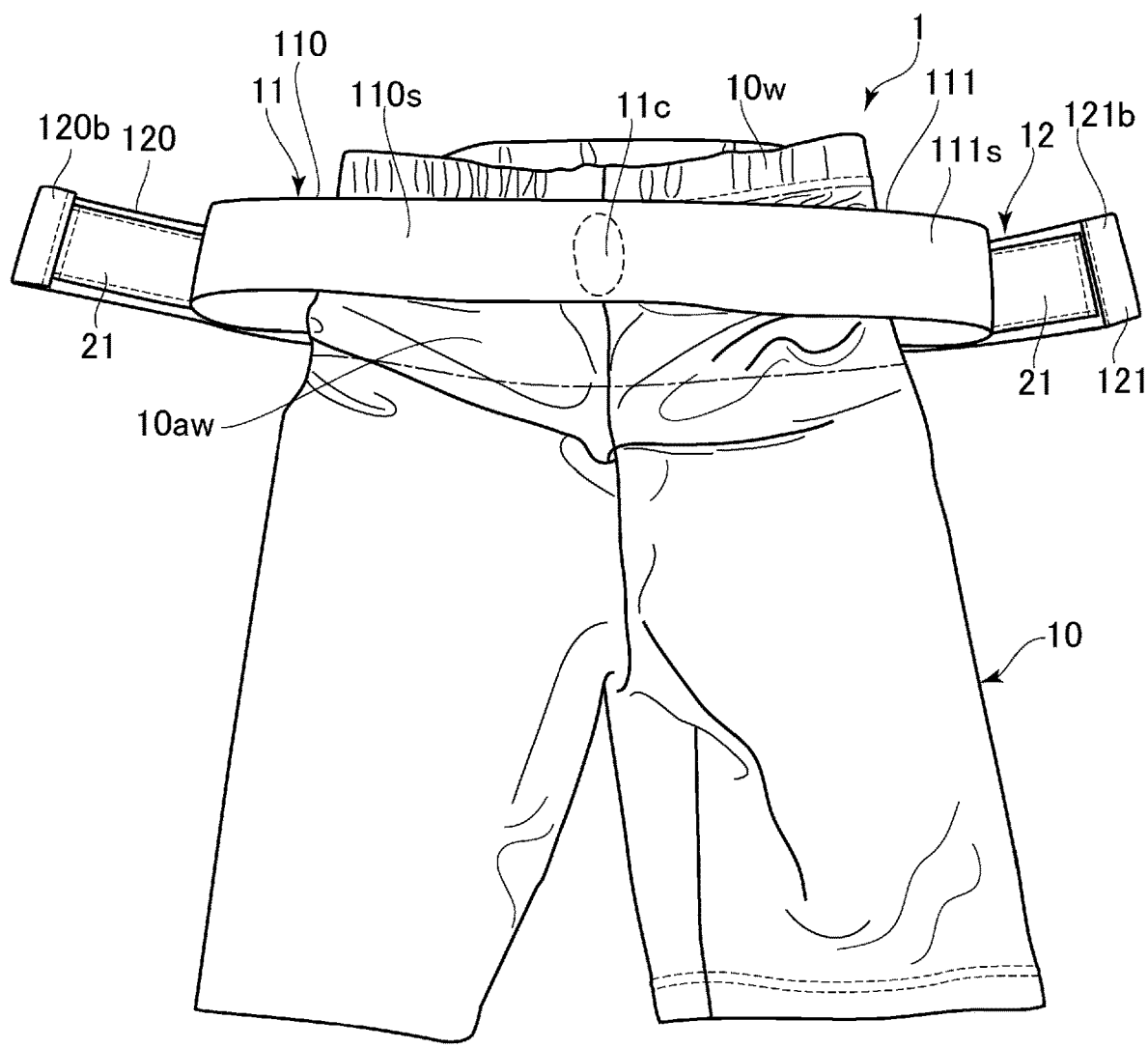
FIG. 5 is a rear view of the pair of belt-attached pants 1 according to the present embodiment.

In addition, FIGS. 4 and 5 are rear views of the pair of belt-attached pants 1 according to the present embodiment. FIG. 4 illustrates a state in which the second belt pieces 120 and 121 are shallowly fastened to the first belt pieces 110 and 111. In addition, FIG. 5 illustrates a state in which the second belt pieces 120 and 121 are deeply fastened to the first belt pieces 110 and 111.

Figure 6:
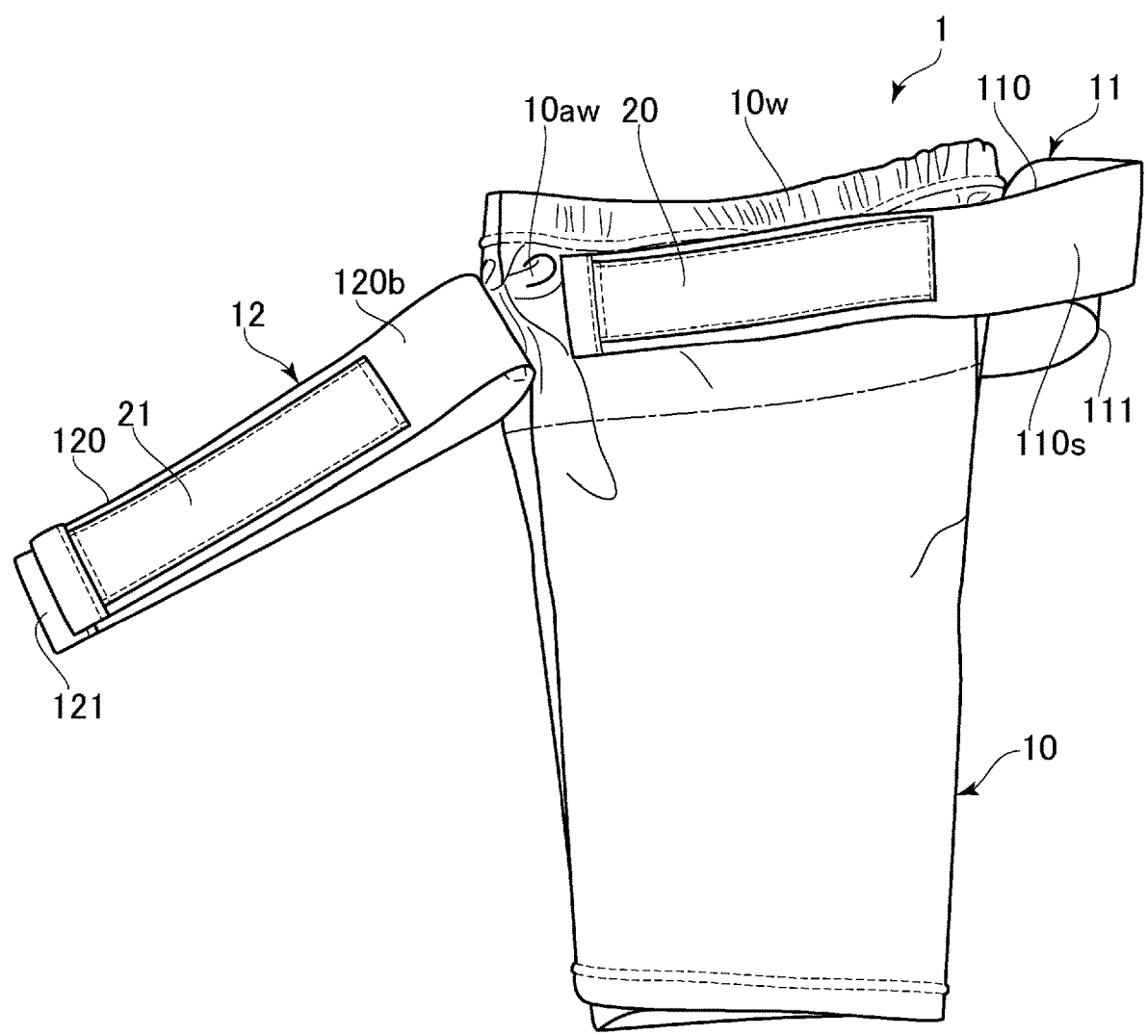
FIG. 6 is a view illustrating one side of the pair of belt-attached pants 1 according to the present embodiment when central parts on the front surface side and the back surface side are respectively pulled outward and folded.
Figure 7:
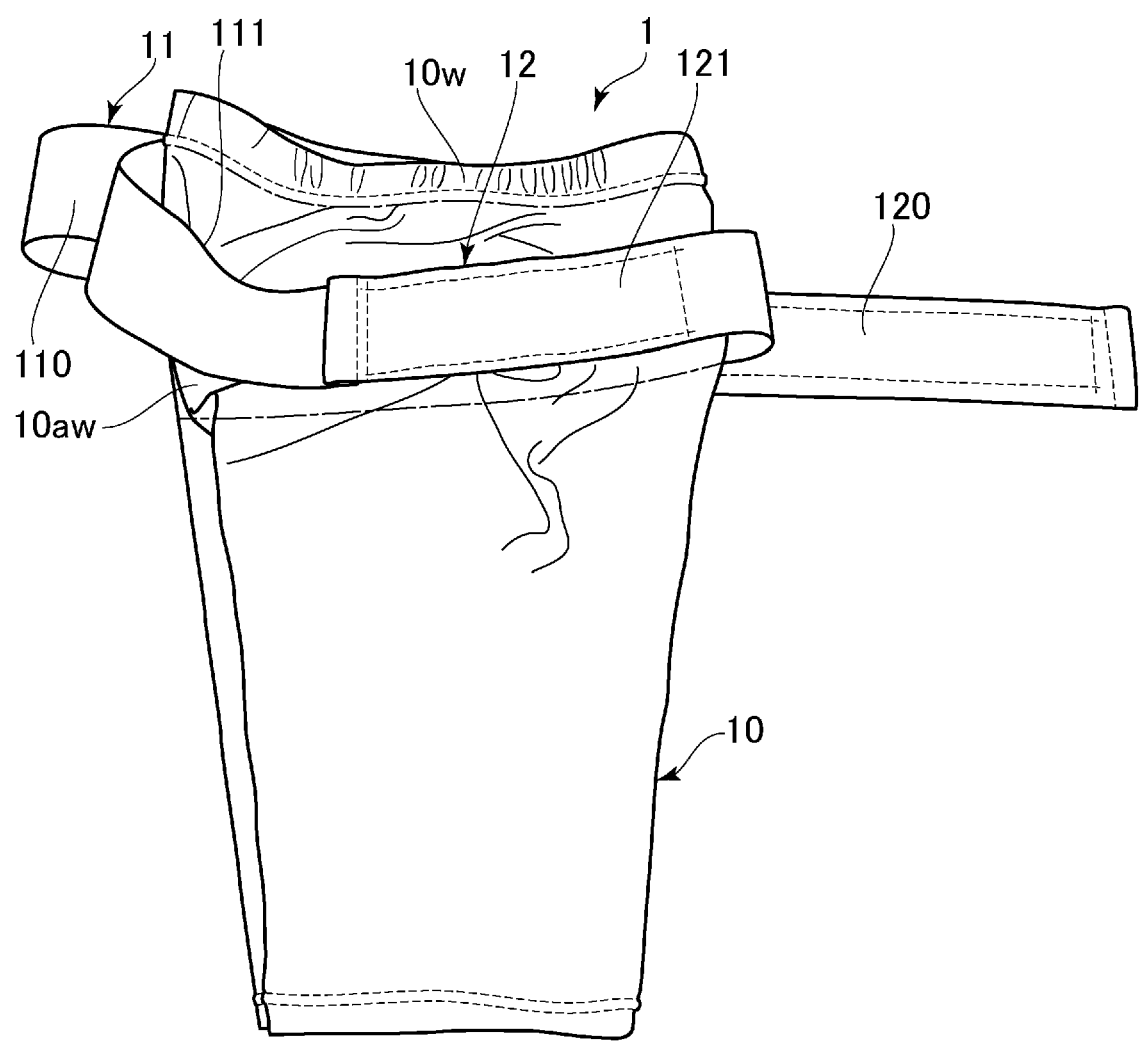
FIG. 7 is a view illustrating a reverse side of the pair of belt-attached pants 1 illustrated in FIG. 6.

In addition, FIG. 6 is a view illustrating one side of the pair of belt-attached pants 1 according to the present embodiment when respective left and right central parts on the front surface side and the back surface side are respectively pulled outward and folded. FIG. 6 illustrates a state in which either of the second belt pieces 120 and 121 are not fastened to the first belt 11. In addition, FIG. 7 is a view illustrating a reverse side of FIG. 6. FIG. 7 illustrates a state in which the second belt piece 121 is fastened to the first belt piece 111.

As illustrated in FIGS. 1 to 7, the pair of belt-attached pants 1 includes a pants main body 10, the first belt 11, and the second belt 12.

In the present embodiment, the pants main body 10 is formed of a pair of trunks-shaped pants formed to have a length such that the lower ends of tubular parts (in the following, referred to as "a leg cover") that individually cover both legs of a wearer (human) reach above the knee when worn (see FIGS. 9 and 10). The pants main body 10 includes a waistband part 10w provided at an upper end part in a freely expanding and contracting manner, and a waist part 10aw that is a tubular part formed below the waistband part 10w and above a crotch 10k (a region sandwiched by alternate long and short dash lines in FIGS. 1, 3, 6, and 7) and covering a lower abdomen above a pubis of the wearer around the waist when worn.

The waistband part 10w is formed by folding back a band-shaped cloth and sewing its open end of the band-shaped cloth to the upper end of the pants main body 10, and has a string hole formed of an inner part of a bellows-shaped part in the waist direction, the bellows-shaped part being folded back and overlapped. Into the string hole, a band-shaped rubber string is inserted, and the diameter of the upper end opening of the pants main body 10 can be expanded and contracted by the elasticity and the bellows shape of the rubber string.

The waist part 10aw is formed of a member having high stretchability with elastic force lower than that of the waistband part 10w. For example, the waist part 10aw is formed of a nylon stretch fabric having excellent stretchability. In the present embodiment, other parts including the cloth part of the waistband part 10w of the pants main body 10 are also formed of a member having similar stretchability.

The first belt 11 includes one belt in a band shape formed of a member having stretchability lower than the stretchability of the waist part 10aw (e.g., a member having an elongation percentage of 0.5% or less when pulled by hand). The first belt 11 of the present embodiment is formed of, for example, a plain weave polyester woven fabric having excellent breaking resistance and dimensional stability, which is used in a vehicle seat belt or the like. In addition, the dimensions are, for example, 50 mm in width and 1.3 mm in thickness.

In the first belt 11, a central part 11c in the longitudinal direction is fixed to a central part on the back surface side of a waist part 10aw by, for example, sewing. The central part 11c may be termed as a first fixed part of the first belt. That is, as illustrated in a circular broken line in FIGS. 4 and 5, most of the central part of the belt 11 is fixed to the pants main body 10. Besides, the first belt pieces 110 and 111, which are two other parts divided into two sides with the central part 11c sandwiched between the first belt pieces 110 and 111, are disposed so as to go around from the back surface side to the front surface side along the waist part 10aw, and parts on the tip end part sides of the first belt pieces 110 and 111 are fixed at a predetermined interval with the central part on the front surface side of the waist part 10aw sandwiched between the parts. The parts on the tip end part sides of the first belt pieces 110 and 111 may be termed as front fixed portions. The tip end parts of the first belt pieces 110 and 111 are disposed to face each other in the waist direction, in each of which the part on the tip end part side is fixed to the pants main body 10 by sewing, for example.

Furthermore, as illustrated in FIGS. 1, 2, and 6, on front surfaces 110s and 111s of the first belt pieces 110 and 111, a fastening female part 20 in a rectangular shape formed of a loop part of a hook-and-loop fastener is provided from a position in the vicinity of each tip end part to a position facing the side of the pants main body 10 (the side of the waist part 10aw).

In the present embodiment, the second belt 12 is formed of one belt in a band shape formed of the similar member to the first belt 11. As illustrated in FIGS. 1 to 3, in the second belt 12, a central part 12c in the longitudinal direction is fixed to the central part on the front surface side of the waist part 10aw by, for example, sewing. That is, as illustrated in a circular broken line in FIGS. 1 to 3, most of the central part of the belt 12 is fixed to the pants main body 10. Besides, the second belt pieces 120 and 121, which are the two other parts divided into two sides with the central part 12c sandwiched between the second belt pieces 120 and 121, are in a non-fixed state. Therefore, when the pair of belt-attached pants 1 is worn, the second belt pieces 120 and 121 hang down to the front surface side of the pants main body 10 by gravity (see FIG. 9). Note that the first belt 11 and the second belt 12 are preferably formed as thin as possible in order that the line of the belt does not stand out through a lower garment when the lower garment is worn on the pair of belt-attached pants 1, for example.

Furthermore, as illustrated in FIGS. 1, 2, and 6, on back surfaces 120b and 121b of the second belt pieces 120 and 121, a fastening male part 21 in a rectangular shape formed of a hook part of a hook-and-loop fastener and having a dimension longer than the fastening female part 20 is provided from the vicinity of the tip end part toward the central part 12c.

With the above configuration, as illustrated in FIG. 2, in the pair of belt-attached pants 1 according to the present embodiment, the second belt piece 120 can be fastened to the first belt piece 110 by fastening the fastening male part 21 of the second belt piece 120 to the fastening female part 20 of the first belt piece 110. Similarly, as illustrated in FIGS. 3, 4, and 7, the second belt piece 121 can be fastened to the first belt piece 111 by fastening the fastening male part 21 of the second belt piece 121 to the fastening female part 20 of the first belt piece 111. As described above, the first belt 11 and the second belt 12 can be connected through the fastening female part 20 and the fastening male part 21.

Besides, the fastening positions of the second belt pieces 120 and 121 can be adjusted by the fastening female part 20 and the fastening male part 21. For example, as illustrated in FIG. 4, the second belt pieces 120 and 121 can be fastened such that the tip end parts of the second belt pieces 120 and 121 are located at end part positions on the central part 11c side of the fastening female parts 20 of the first belt pieces 110 and 111. In addition, as illustrated in FIG. 5, the second belt pieces 120 and 121 can be fastened such that the tip end parts of the second belt pieces 120 and 121 are located at positions beyond the end part position on the central part 11c side of the fastening female parts 20 of the first belt pieces 110 and 111. The fastening position can be adjusted stepwise including locations between these positions.

Figure 8:
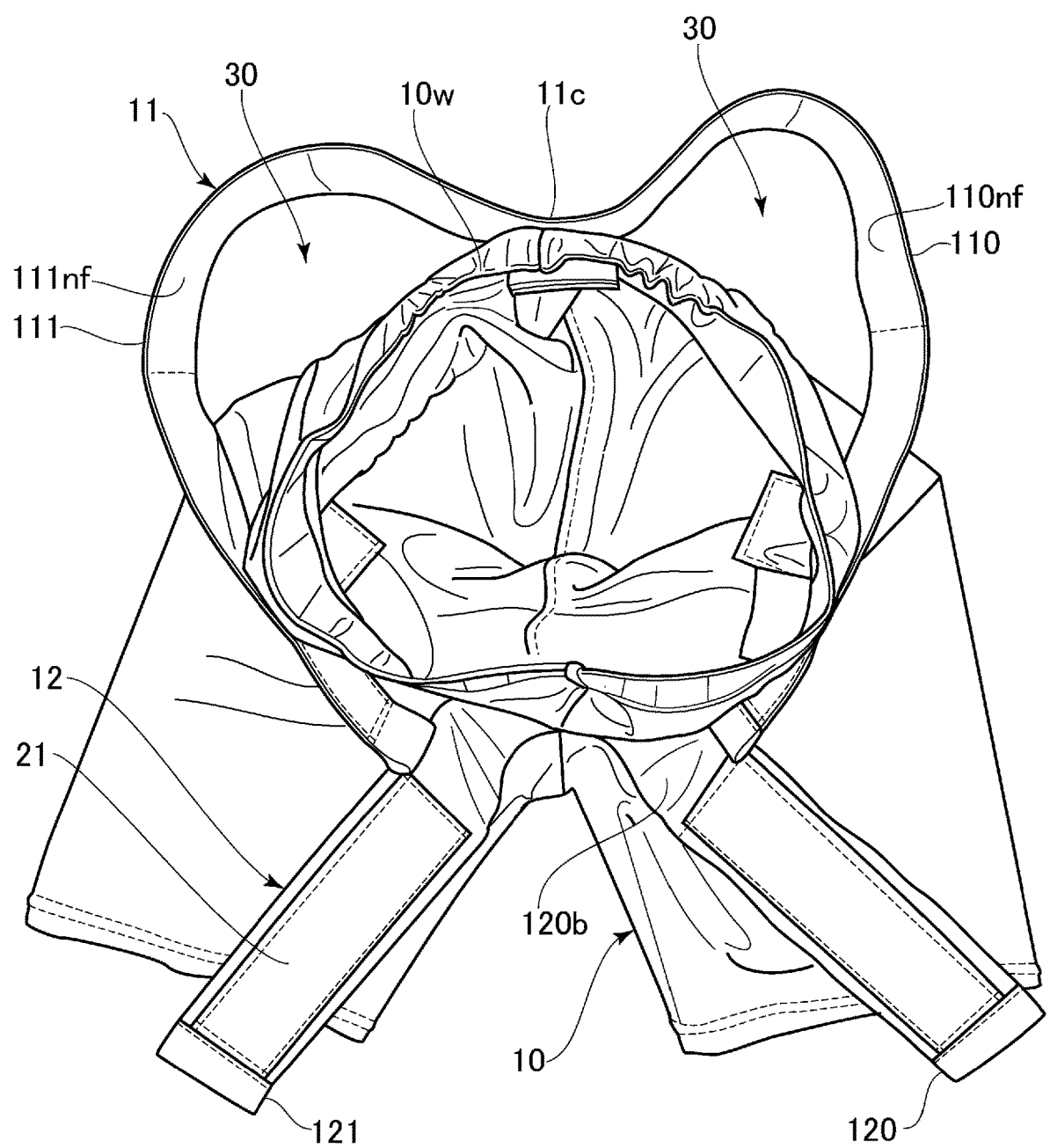
FIG. 8 is a view of the pair of belt-attached pants 1 according to the present embodiment placed flat, as seen in a plan view, a part, above a waist part 10aw, of the belt-attached pants 1 being folded.

Here, FIG. 8 is a view of the pair of belt-attached pants 1 according to the present embodiment placed flat, as seen in a plan view, a part, above the waist part 10aw, of the belt-attached pants 1 being folded. FIG. 8 illustrates a state in which either of the second belt pieces 120 and 121 are not fastened to the first belt 11.

As illustrated in FIG. 8, only the parts on the tip end part side of the first belt pieces 110 and 111 are fixed, and the other parts are not fixed. That is, the first belt pieces 110 and 111 have non-fixed parts 110nf and 111nf that are not fixed to the waist part 10aw. These non-fixed parts 110nf and 111nf are each formed to have a dimension longer than the length dimension of the part, facing each of the non-fixed parts 110nf and 111nf, of the waist part 10aw in a non-stretched state. As a result, a gap 30 is generated between the pants main body 10 not worn and each of the non-fixed parts 110nf and 111nf. That is, the stretch in the radial direction of the waist part 10aw is allowed by the gap 30.

[Operation]

Next, the operation of the present embodiment will be described.

Figure 9:
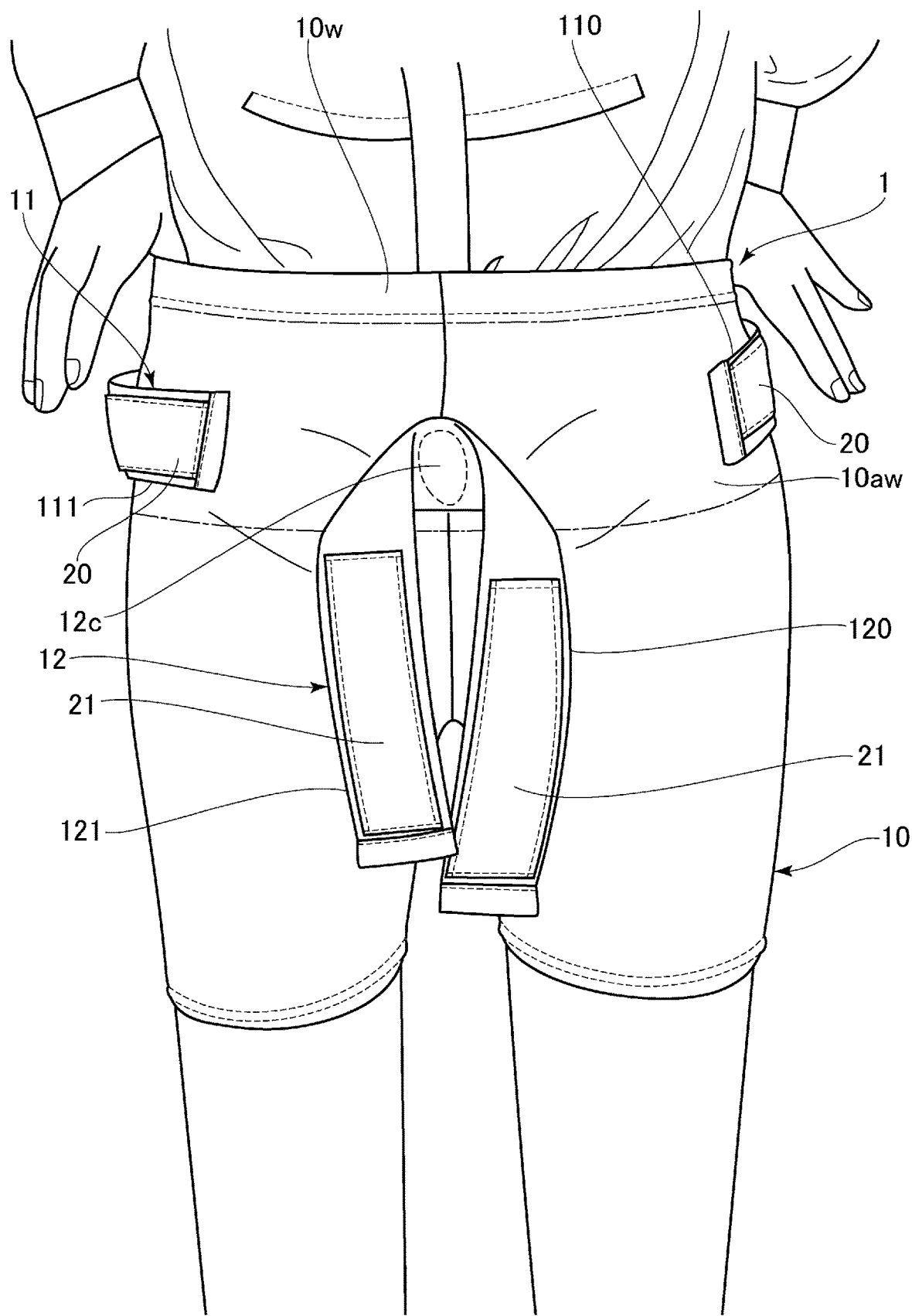
FIG. 9 is a view illustrating a part of a person wearing the pair of belt-attached pants 1 according to the present embodiment.
Figure 10:
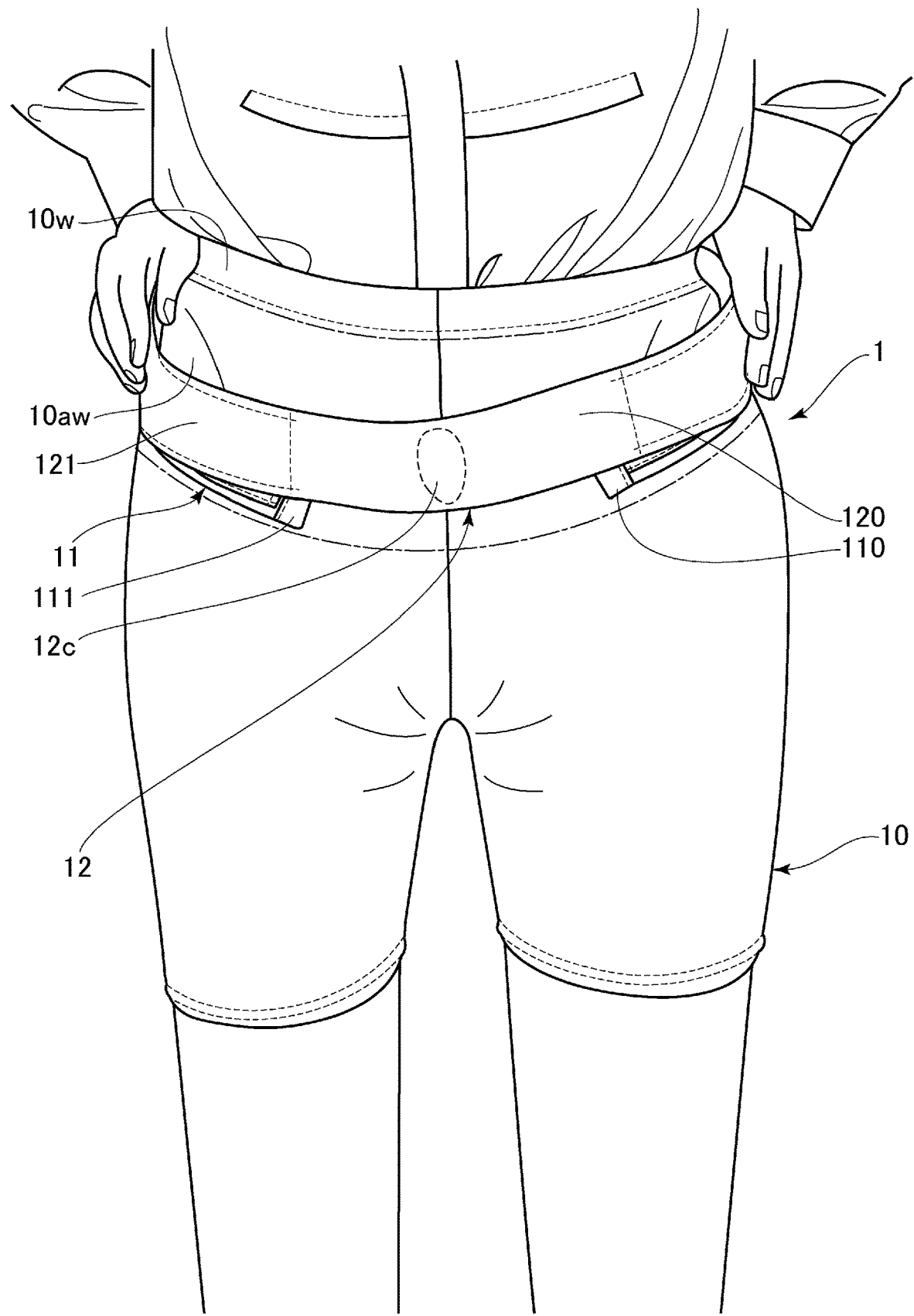
FIG. 10 is a view illustrating a part of the person wearing the pair of belt-attached pants 1 according to the present embodiment.

Here, FIGS. 9 and 10 are front views illustrating a part of a person wearing the pair of belt-attached pants 1 according to the present embodiment. FIG. 9 illustrates a state in which either of the second belt pieces 120 and 121 are not fastened to the first belt 11. In addition, FIG. 10 illustrates a state in which both of the second belt pieces 120 and 121 are fastened to the first belt pieces 110 and 111.

Figure 11:
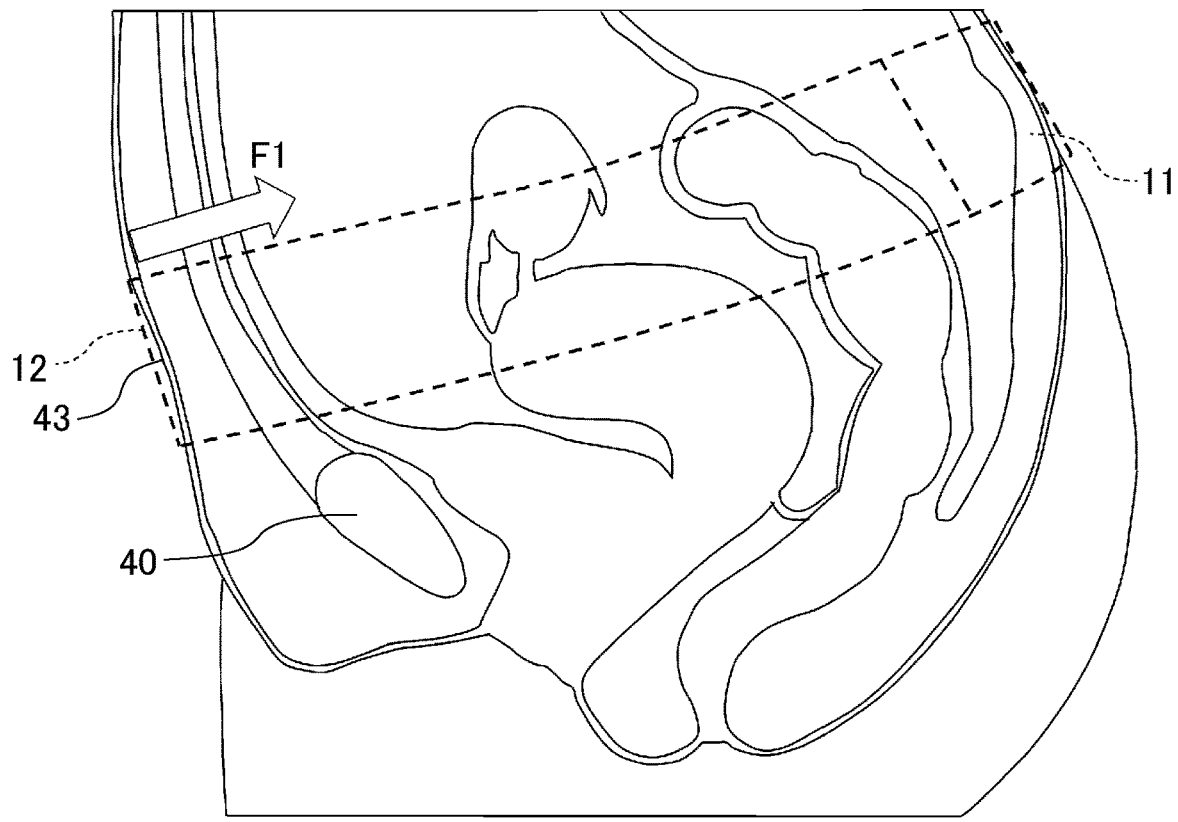
FIG. 11 is a partial sectional view of the lower body of a woman.
Figure 12:
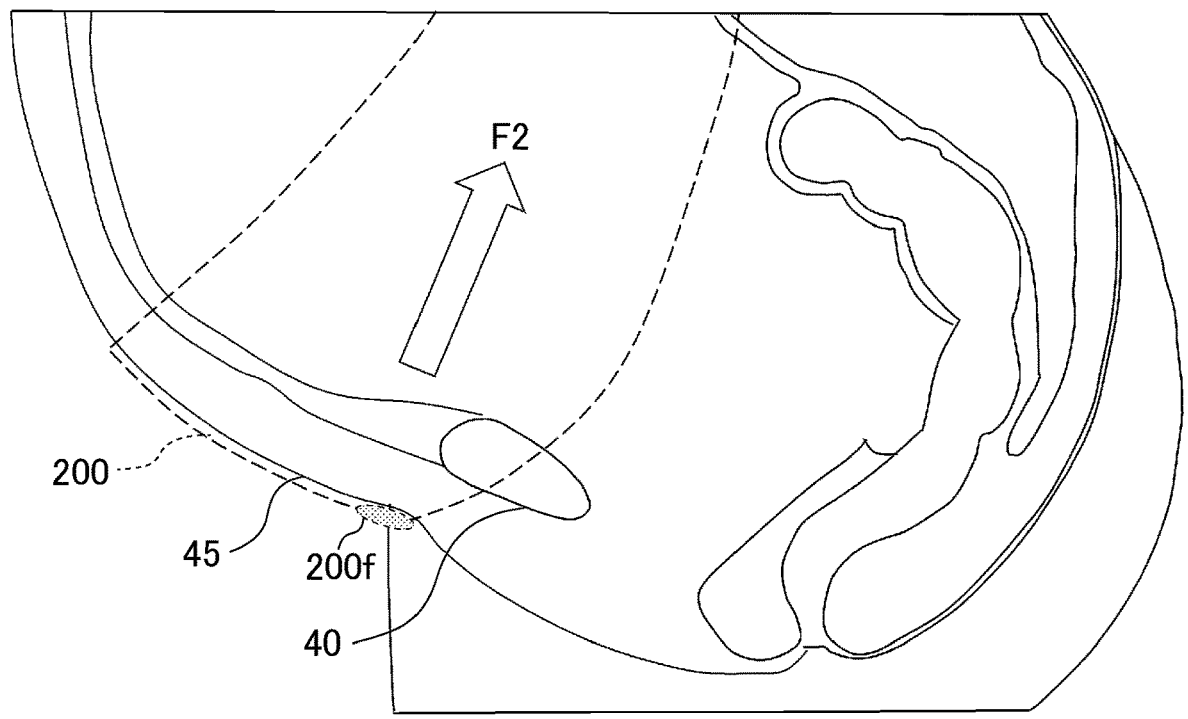
FIG. 12 is a partial sectional view of the lower body of a woman in a state in which the abdomen is swollen due to pregnancy.

In addition, FIG. 11 is a partial sectional view of the lower body of a woman. In FIG. 11, the tightening position (belt position) of the pair of belt-attached pants 1 according to the present embodiment is indicated by a broken line, and the direction of the tightening force of the pair of belt-attached pants 1 is indicated by an arrow. In addition, FIG. 12 is a partial sectional view of the lower body of a woman in a state in which the abdomen is swollen due to pregnancy. In FIG. 12, the tightening position of the pair of belt-attached pants 200 of the conventional art is indicated by a broken line, and the direction of the tightening force of the pair of belt-attached pants 200 is indicated by an arrow.

When the pair of belt-attached pants 1 is to be worn, first, the legs are individually put into the inside of tubular parts 5 of the leg cover in a state in which the rubber string of the waistband part 10w is extended to increase the opening diameter. At this time, since the waist part 10aw is also formed of a member having high stretchability, the waist part 10aw extends in the radial direction by the length 10 difference between the non-fixed parts 110nf and 111nf of the first belt 11. As a result, the legs can be easily put through together with the expanded state of the waistband part 10w.

Subsequently, when both legs are put into the leg cover and then the waistband part 10w is pulled upward to release 15 the stretched state of the rubber string, as illustrated in FIG. 9, the waistband part 10w fits around the waist by the elastic force of the rubber string. Besides, the waist part 10aw covers the lower abdomen above the pubis around the waist part, and the pair of belt-attached pants 1 is worn. 20

In addition, as illustrated in FIG. 9, the waist part 10aw stretches according to the body shape of the wearer by wearing the pair of belt-attached pants 1. As a result, the distance between the first belt pieces 110 and 111 and the second belt pieces 120 and 121 changes. On the other hand, 25 since the fastening female part 20 and the fastening male part 21 are formed of hook-and-loop fasteners formed in a rectangular shape along the longitudinal direction, the fastening position of the fastening male part 21 can be adjusted according to the body shape of the wearer. 30

As illustrated in FIG. 10, the second belt pieces 120 and 121 are fastened to the first belt pieces 110 and 111, and thus the first belt 11 and the second belt 12 formed of a member having low stretchability are connected, and the lower abdomen above the pubis is tightened along the waist part 35 10aw and the waist part is in a fixed state.

In this state, as indicated by a broken line in FIG. 11, the central part 12c of the second belt 12 and the central part on the front surface side of the waist part 10aw are located at the position of a suprapubic region 43 above a pubis 40, and 40 the first belt 11 and the second belt 12 are connected along the part covered by the waist part 10aw. At this time, tightening force F1 is generated in a direction substantially perpendicular to the belt surface. Note that an arrow in FIG. 11 indicating the tightening direction of the tightening force 45 F1 indicates the direction of the tightening force generated in the central part 12c.

In addition, the tightening force F1 can be adjusted by adjusting the fastening position of the fastening male part 21. Specifically, by adjusting the fastening positions of the 50 second belt pieces 120 and 121 in a state in which the lower abdomen is recessed, the degree of tightening of the lower abdomen can be adjusted.

For example, as illustrated in FIG. 4, the second belt pieces 120 and 121 are fastened at shallow positions on the 55 tip end sides of the first belt pieces 110 and 111, and thus the tightening force can be weakened. On the other hand, as illustrated in FIG. 5, the second belt pieces 120 and 121 are fastened at deep positions on the central part 11c side of the first belt pieces 110 and 111, and thus the tightening force 60 can be increased.

Note that, as illustrated in FIG. 12, in the pair of belt-attached pants 200 of the conventional art, the central part of the belt is located at the central position on the pants front surface side of a lower abdomen 45 bulging forward from 65 the lower position of the pubis 40, and although not illustrated, both end parts of the belt are respectively fastened at the pants side positions above the pelvis. As indicated by an arrow indicating the tightening direction of tightening force F2 in the drawing, the tightening force F2 is generated in a direction in which the lower abdomen 45 is lifted upward from the lower side. That is, instead of tightening the bulging abdomen due to pregnancy in the direction opposite to the bulging direction, the abdomen is supported so as to be lifted from the lower side like a hammock. In addition, in the central part of the belt, only the lower end part is laterally fixed at a fixed position 200f in FIG. 12, and the other parts are not fixed. That is, the pants can be worn in a state in which the entire belt portion is tilted forward, and both end parts can be fastened by lifting the abdomen bulging at the belt portion so as to wrap the abdomen from the lower side after being worn in this state. However, since only the lower end part is fixed for this function, the strength in a state in which both end parts are not fastened is weaker than that in the case in which almost the entire central part is fixed, for example.

Effects of Embodiment

Next, effects of the present embodiment will be described.

In the present embodiment, the pair of belt-attached pants 1 is formed including: the pants main body 10 having the tubular waist part 10aw that has stretchability and covers the lower abdomen above the pubis around the waist when worn; and the first belt 11 in which the central part 11c in the longitudinal direction is fixed to the central part on the back surface side of the waist part 10aw. Here, in the first belt 11, the first belt pieces 110 and 111, which are two other parts divided into two sides with the central part 11c sandwiched between the first belt pieces 110 and 111, go around from the back surface side to the front surface side of the waist part 10aw, and are fixed to the front surface side of the waist part 10aw at a predetermined interval. Besides, the pair of belt-attached pants 1 is formed including the second belt 12 in which the central part 12c is fixed to the central part on the front surface side of the waist part 10aw, and the second belt pieces 120 and 121, which are the two other parts divided into two sides with the central part 12c sandwiched between the second belt pieces 120 and 121, each have a length extending to each of both sides of the waist part 10aw along the waist part 10aw on the side where each of the second belt pieces 120 and 121 separates from the central part 12c. Furthermore, the pair of belt-attached pants 1 is formed including the fastening female part 20 and the fastening male part 21 that enable the second belt piece 120 to be fastened to the first belt piece 110 and enable the second belt piece 121 to be fastened to the first belt piece 111. Here, the fastening female parts 20 are provided on the front surfaces 110s and 111s of the first belt pieces 110 and 111, respectively, and the fastening male parts 21 are provided on the back surfaces 120b and 121b of the second belt pieces 120 and 121, respectively.

With such a configuration, after the pair of belt-attached pants 1 is worn, the fastening male part 21 of the second belt piece 120 can be fastened to the fastening female part 20 of the first belt piece 110, and the fastening male part 21 of the second belt piece 121 can be fastened to the fastening female part 20 of the first belt piece 111. As a result, since the lower abdomen above the pubis can be tightened around the waist by the first belt 11 and the second belt 12, it is possible to suppress the expansion of the abdominal wall for the lower abdomen above the pubis and to fix the waist. As a result, for example, it is possible to suppress the bulging of the lower abdomen (sticking out abdomen) due to the opening of the pelvis and the looseness of the lower abdomen after delivery. Besides, it is possible to suppress the bulging of the lower abdomen (sticking out abdomen) due to the looseness of the pelvic floor muscle, the abdominal wall muscle, and the like regardless of the gender, and it is possible to effectively perform an exercise for eliminating the looseness of the abdominal wall muscle. Furthermore, since the first and second belts 11 and 12 are fixed to the pants main body 10, it is possible to make the belts less likely to be displaced from a point at which the lower abdomen is desired to be pressed. Furthermore, since the second belt 12 is formed not to interfere with the part (crotch 10k) covering the lower side from the pubis of the pants main body 10, it is possible to easily provide the front opening, the chuck, and the like for men.

Besides, the first belt pieces 110 and 111 are formed to have equal lengths, and the second belt pieces 120 and 121 are formed to have equal lengths. Furthermore, the central part 12c of the second belt 12 is fixed to a part of the waist part 10aw covering the central part of the lower abdomen above the pubis when worn. As a result, it is possible to position the central part 12c of the second belt 12 at the central part of the lower abdomen of the wearer wearing the pair of belt-attached pants 1. Besides, since the second belt pieces 120 and 121 are formed to have an equal length with the central part 12c sandwiched between the second belt pieces 120 and 121, the second belt pieces 120 and 121 are fastened to the first belt pieces 110 and 111 with the central part of the lower abdomen as the center, and thus it is possible to easily tighten the lower abdomen in a well-balanced manner.

In addition, in the present embodiment, the first and second belts 11 and 12 are formed of a member having stretchability lower than that of the waist part 10aw.

With such a configuration, it is possible to tighten the lower abdomen above the pubis around the waist by the first belt 11 and the second belt 12 formed of a member having stretchability lower than that of the waist part 10aw. As a result, since the lower abdomen above the pubis can be tightened more firmly around the waist, the expansion of the abdominal wall can be more firmly suppressed, and it is possible to increase the abdominal pressure. As a result, it is possible to further enhance the effect of muscle strength training of the abdominal wall muscles, and it is possible to stabilize the trunk to reduce the burden on the body such as the waist during exercise, housework, and work.

In addition, in the present embodiment, the fastening female parts 20 and the fastening male parts 21 are configured such that each of the second belt pieces 120 and 121 of the second belt 12 can be fastened at a given position along the longitudinal direction of corresponding one or the other of the first belt pieces 110 and 111 of the first belt 11. As a result, it is possible to adjust the fastening position of each of the second belt pieces 120 and 121 at a given position along the longitudinal direction of the corresponding first belt piece 110 or 111. As a result, since the force that tightens the lower abdomen can be adjusted stepwise by adjusting the fastening position, for example, it is easy to tighten the lower abdomen with the best tightening force suitable for the user.

In addition, in the present embodiment, there are provided the non-fixed parts 110nf and 111nf that are parts other than parts of the tip end sides of the first belt pieces 110 and 111 and are not fixed to the pants main body 10. Besides, the non-fixed parts 110nf and 111nf are each formed to have a dimension longer than the length of the part, facing each of the non-fixed parts 110nf and 111nf, of the waist part 10aw in a non-stretched state. As a result, the waist part 10aw can be extended by the dimension of the difference between each of the non-fixed parts 110nf and 111nf and the part, facing each of the non-fixed parts 110nf and 111nf, of the waist part 10aw. As a result, since the upper opening side of the pair of belt-attached pants 1 can be widened by the dimension of the difference, it is possible to easily wear the pair of belt-attached pants 1.

In addition, in the present embodiment, the first and second belts 11 and 12 are formed of a polyester woven fabric, and the fastening female part 20 and the fastening male part 21 are formed of hook-and-loop fasteners. As a result, since a hard part such as a metal part is not used as a component for tightening the lower abdomen, there is no necessity to worry about an injury due to the component even when worn in performing various sports games such as rugby, judo, and jump, and various exercises such as muscle strength training, jogging, and running.

In addition, in the present embodiment, the central part 12c of the second belt 12 is fixed to the central part on the front surface side of the waist part 10aw, and the second belt pieces 120 and 121 are in the non-fixed state. As a result, when the second belt pieces 120 and 121 are not fastened, the second belt pieces 120 and 121 are in the state of hanging down toward the front surface side and can be visually observed, and thus it is easy to avoid contamination, for example, at the time of using a toilet.

In addition, in the present embodiment, most of the central part 11c of the first belt 11 and the central part 12c of the second belt 12 are fixed at a position above the part, covering the pubis, of the pants main body 10. As a result, as compared with the conventional configuration in which only the lower end part of the central part of the belt is fixed to the crotch 10k of the pants main body, it is possible to easily provide the front opening and the chuck for men and also to shorten the belt portion that hangs forward. As a result, it is possible to more easily taking off and putting on the pants, for example, when using a toilet. In addition, it is possible to increase strength such as tensile strength as compared with the conventional art.

[Correspondence Relationship]

In the present embodiment, the first belt pieces 110 and 111 correspond to the two first other parts of inventions 1, 4, and 5, the second belt pieces 120 and 121 correspond to the two second other parts of invention 1 or 4 or the two other parts of invention 6, and the fastening female part 20 and the fastening male part 21 correspond to the fastening parts of inventions 1, 4, and 6.

Modified Example

In the above-described embodiment, although an example is described in which the pants main body 10 is formed of a pair of trunks-shaped pants, the present invention is not limited to this configuration. In addition, the pants main body 10 may be formed of other types of pants such as a girdle type, a brief-type, a culotte-type, and a legging type, and may be applied not only to underwear but also to a lower garment such as slacks, chino pants, cargo pants, gymnastics pants, and jersey pants. In this case, in the case in which the first belt 11 and the second belt 12 are not hidden by an outerwear or the like, the first belt 11 the second belt 12 are exposed to the outside. Therefore, it is desirable to form the first belt 11 and the second belt 12 of those having high design characteristics, for example. In addition, the pants main body 10 may include, for example, support tights worn under the lower garment by a competitor, a climber, or the like.

In addition, in the above-described embodiment and the modified examples of the embodiment, although an example is described in which the first belt 11 and the second belt 12 are fixed to the pants main body 10 by sewing, the present invention is not limited to this configuration. For example, the first belt 11 and the second belt 12 may be fixed by another method such as fixing using an adhesive or the like. Alternatively, the first belt 11 and the second belt 12 may be formed attachable and detachable by a fastener such as a hook-and-loop fastener.

In the above-described embodiment and the modified examples of the embodiment, although an example is described in which the pants main body 10 is mainly formed of a nylon fabric, the present invention is not limited to this configuration. As long as the stretchability of the waist part 10aw can be secured, the waist part 10aw may be formed of a woven fabric using other synthetic fibers, a woven fabric using natural fibers such as cotton, hemp, silk, and wool, or a woven fabric formed of a yarn obtained by blending natural fibers and synthetic fibers. Alternatively, a plurality of types of woven fabrics may be combined.

In the above-described embodiment and the modified examples of the embodiment, although an example is described in which the first belt 11 and the second belt 12 are formed of a polyester woven fabric having a low elongation percentage, the present invention is not limited to this configuration. For example, when it is possible to form a woven fabric having a sufficient anti-elongation property (low elongation percentage property) to tighten the lower abdomen, the woven fabric may be formed of other synthetic fibers or natural fibers. In addition, the first belt 11 and the second belt 12 may be formed of a woven fabric made of a yarn obtained by blending a plurality of fibers, or may be formed by combining a plurality of types of woven fabrics. In addition, the material is not limited to a woven fabric, and may be formed of another material such as leather as long as the material has sufficient anti-elongation property to tighten the lower abdomen.

In addition, in the above-described embodiment and the modified examples of the embodiment, although the entire waist part 10aw is formed of a member having high stretchability, the present invention is not limited to this configuration. For example, other configurations may be provided, such as a configuration in which a part or all of the front surface side of the waist part 10aw is formed of a member having low stretchability. In addition, in the case in which this configuration is provided, a configuration may be provided in which the non-fixed parts 110nf and 111nf may not be provided in the first belt 11. In addition, in the case in which the non-fixed parts 110nf and 111nf are not provided, a configuration may be provided in which the entire first belt 11 is fixed to the pants main body 10. In addition, even in the case in which the entire waist part 10aw is formed of a member having high stretchability, a configuration may be provided in which the entire first belt 11 is fixed to the pants main body 10 without providing the non-fixed parts 110nf and 111nf.

In the above-described embodiment and the modified examples of the embodiment, the fixing places of the first belt 11 and the second belt 12 are not limited to the central parts 11c and 12c, and may be other positions.

In addition, in the above-described embodiment and the modified examples of the embodiment, the fixing positions of the first belt 11 and the second belt 12 are not limited to the central part on the back surface side and the central part on the front surface side of the waist part 10aw, and may be other positions on the back surface side and other positions on the front surface side within the range of the waist part 10aw.

In addition, in the above-described embodiment and the modified examples of the embodiment, although the dimensions of the width of 50 mm and the thickness of 1.3 mm are described as examples of the dimensions of the first belt 11 and the second belt 12, the present invention is not limited to this configuration. For example, other width dimensions may be used without departing from the range of the waist part 10aw. In addition, other thickness dimensions may be used as long as necessary tightening performance and durability can be obtained.

In addition, in the above-described embodiment and the modified examples of the embodiment, the configuration is taken as an example and described in which the second belt pieces 120 and 121 of the second belt 12 are fastened to the first belt pieces 110 and 111 of the first belt 11 through the fastening female part 20 and the fastening male part 21 formed of the loop part and the hook part of the hook-and-loop fastener, respectively. The present invention is not limited to this configuration, and a configuration may be provided in which the loop part and the hook part are interchanged, or a configuration may be provided in which a fastener other than a hook-and-loop fastener is used for fastening. As the fastener other than the hook-and-loop fastener, for example, a configuration may be provided in which a component having a pointed claw part at the tip, which is used for bandage fixing or the like, is provided on each of the belt pieces of one of the first belt 11 and the second belt 12, and the claw part of the claw component provided on each of the belt pieces of the one is hooked on the front surface or the back surface of each of the belt pieces of the other of the first belt 11 and the second belt 12 so as to fix the belt pieces of the one to the belt pieces of the other. In addition, the present invention is not limited to the claw component, and other configurations may be provided, such as a configuration in which a button hole is provided in each belt piece of one of the first belt 11 and the second belt 12, a button is provided in each belt piece of the other of the first belt 11 and the second belt 12, and each belt piece of the one is fastened to each belt piece of the other through the button, or a configuration in which each belt piece of one belt is fastened to each belt piece of the other belt through an independent fastener.

In the above embodiment and the modified examples of the embodiment, although the first belt 11 and the second belt 12 are connected to tighten the lower abdomen above the pubis, the present invention is not limited to this configuration. For example, without providing the first belt 11, the other part except for a part of the front surface side of the waist part 10aw is formed of a member having low stretchability equivalent to the first belt 11. Besides, a configuration may be provided in which the fastening female parts 20 are provided on both side parts of the waist part 10aw of the pants main body 10, and the fastening male parts 21 of the second belt pieces 120 and 121 of the second belt 12 are fastened to the fastening female parts 20. With this configuration, a place of a low stretchability of the waist part 10aw exerts the same function as the first belt 11, and the lower abdomen above the pubis can be firmly tightened.

In the above-described embodiment and the modified examples of the embodiment, the configuration is described in which the second belt pieces 120 and 121 of the second belt 12 are not fixed, and the fastening male parts 21 of the second belt pieces 120 and 121 are fastened to the fastening female parts 20 of the first belt pieces 110 and 111 of the first belt 11. The present invention is not limited to this configuration, and for example, the entire second belt pieces 120 and 121 are fixed to the pants main body 10, and the first belt pieces 110 and 111 are not fixed. Besides, a configuration may be provided in which the fastening female parts 20 (or the fastening male parts 21) are provided on the back sides of the first belt pieces 110 and 111, the fastening male parts 21 (or the fastening female parts 20) are provided on the front surfaces of the second belt pieces 120 and 121, and the fastening female parts 20 (or the fastening male parts 21) of the first belt pieces 110 and 111 are fastened to the fastening male parts 21 (or the fastening female parts 20) of the second belt pieces 120 and 121. In addition, in the case in which this configuration is provided, for example, the second belt 12 is not provided, and the other part except for a part of the back surface side of the waist part 10$aw$ is formed of a member having low stretchability equivalent to the second belt 12. Besides, a configuration may be provided in which the fastening male parts 21 (or the fastening female parts 20) are provided on both side parts of the waist part 10$aw$ of the pants main body 10, and the fastening female parts 20 (or the fastening male parts 21) of the first belt pieces 110 and 111 of the first belt 11 are fastened to the fastening male parts 21 (or the fastening female parts 20). With this configuration, a place of a low stretchability of the waist part 10$aw$ exerts the same function as the second belt 12, and the lower abdomen above the pubis can be firmly tightened.

In addition, in the above-described embodiment and the modified examples of the embodiment, the crotch 10$k$ of the pants main body 10 may be provided with a front opening, a chuck, and the like to form a pair of male belt-attached pants. In the case in which this configuration is provided, it is possible to carry out urination without taking off the pants and in a state in which the second belt 12 is fastened, at the time of urination in the toilet.

In addition, in the above-described embodiment and the modified examples of the embodiment, for example, a configuration may be provided in which in consideration of the case in which the pair of belt-attached pants 1 is worn by a person who is obese and whose abdomen greatly bulges, a third belt formed of a relatively soft material is provided above the first belt 11 and the second belt 12. With this configuration, the abdomen hanging down from above the part tightened by the first belt 11 and the second belt 12 can be supported by the third belt. The third belt can be formed of a material wider and softer than the materials of the first belt 11 and the second belt 12 in a configuration in which two belts are connected to each other similarly to the set of the first belt 11 and the second belt 12. Alternatively, a configuration can be provided in which the third belt is formed of a material wider and softer than the material of the second belt 12 in a configuration similar to the second belt and both end parts of the second belt are each fastened to the fastening female part provided on the side part of the pants main body. Other configurations may be provided as long as the abdomen hanging down from above can be supported with no pressure.

Figure 13:
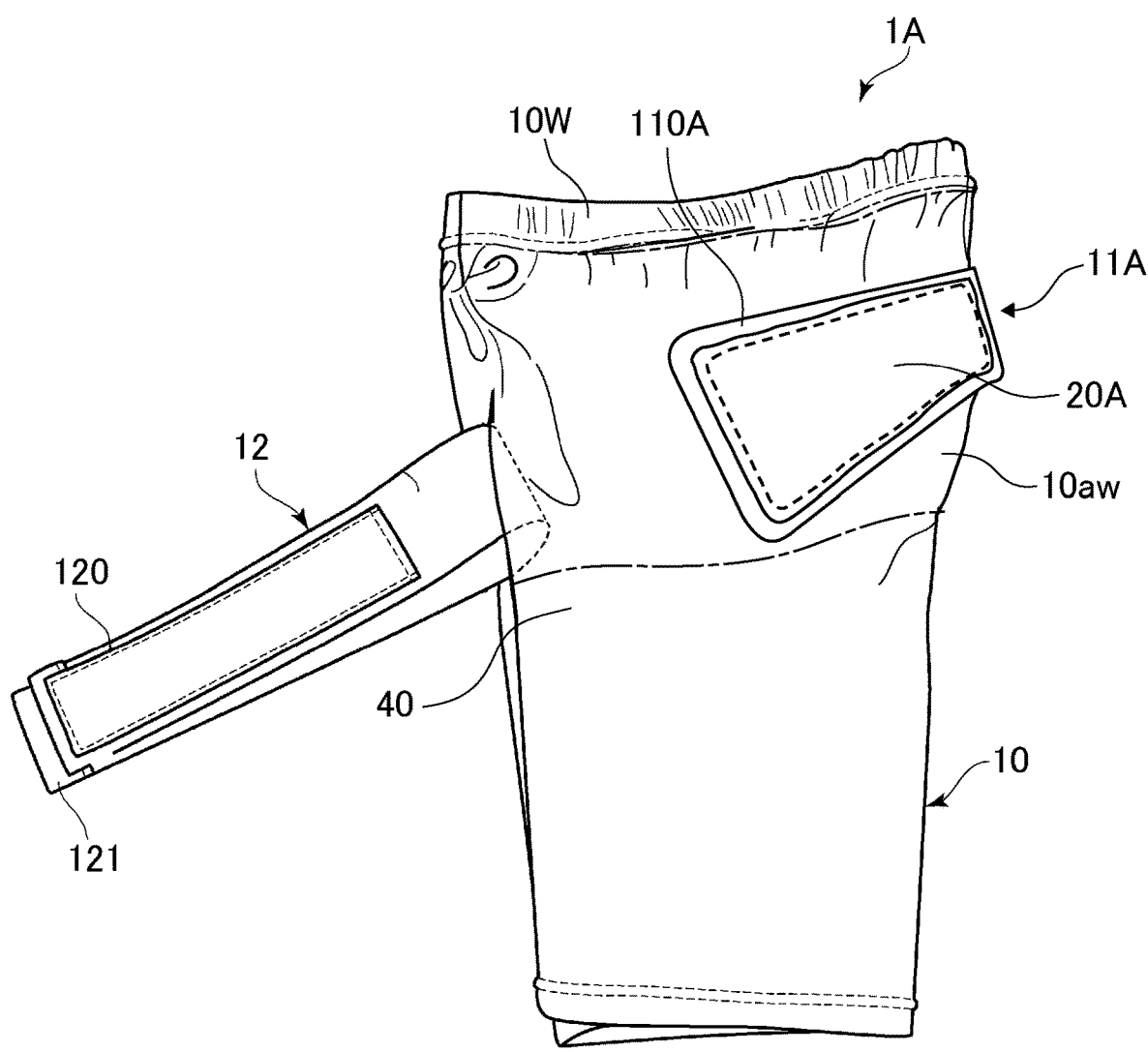
FIG. 13 is a view illustrating one side when a pair of belt-attached pants 1A according to a modified example is folded by pulling the central parts on the front surface side and the back surface side outward respectively.

In addition, in the above-described embodiment and the modified examples of the embodiment, a configuration may be provided in which, for example, as in a pair of belt-attached pants 1A illustrated in FIG. 13, the fixing position of the second belt 12 is fixed below the fixing position (see FIG. 6) of the pair of belt-attached pants 1 of the above-described embodiment and the modified examples within the range of the waist part 10$aw$, which is the range sandwiched by alternate long and short dashed lines in FIG. 13. Here, FIG. 13 is a view illustrating one side of the pair of belt-attached pants IA according to the modified example when the central parts on the front surface side and the back surface side are respectively pulled outward and folded. FIG. 13 illustrates a state in which either of the second belt pieces 120 and 121 of the second belt 12 are not fastened to the first belt 11A. Note that the fixing position is not limited to the fixing position illustrated in FIG. 13, and the fixing position may be another position as long as the fixing position is within the range of the waist part 10$aw$.

In addition, in the above-described embodiment and the modified examples of the embodiment, a configuration may be provided in which, for example, as illustrated in the first belt 11A of the pair of belt-attached pants IA illustrated in FIG. 13, the width of the first belt pieces 110A and 111A (not illustrated) is wider than the width (see FIG. 6) of the first belt pieces 110 and 111 of the pair of belt-attached pants 1 of the first embodiment. In the example illustrated in FIG. 13, a first belt piece 110A is formed to gradually increase in width from the back surface side toward the front surface side, and is formed to have about twice the width at the front surface side end part. As a result, the fastening position in the up-down direction can be adjusted. Note that the present invention is not limited to this configuration, and the width may be constant at about twice the width, or may be other widths with no limitation to about twice the width.

In the above-described embodiment and the modified examples of the embodiment, although the gap 30 is provided between the first belt pieces 110 and 111 of the first belt 11 and the pants main body 10, the present invention is not limited to this configuration. For example, as illustrated in a first belt 11A of the pair of belt-attached pants 1A illustrated in FIG. 13, a configuration may be provided in which the entire first belt piece is fixed to the pants main body 10 without providing a gap (gap 30 in FIG. 8) between the first belt piece and the pants main body 10.

The entire contents of Japanese Patent Application No. 2020-36033 (filed on Mar. 3, 2020), from which the present application claims priority, are incorporated herein by reference.

Here, although the description is made with reference to a limited number of embodiments, the scope of rights is not limited to the embodiments, and modifications of the embodiments based on the above disclosure are obvious to those skilled in the art.

LIST OF REFERENCE NUMERALS 1, 1A . . . Belt-attached pants
10 . . . Pants main body
10$w$ . . . Waistband part
10$aw$ . . . Waist part
11, 11A . . . First belt
11$c$, 12$c$ . . . Central part
12 . . . Second belt
20, 20A . . . Fastening female part
21 . . . Fastening male part
40 . . . Pubis
43 . . . Suprapubic region
110, 111, 110A, 111A . . . First belt piece
110$s$, 111$s$ . . . Front surface of first belt pieces 110 and 111
120, 121 . . . Second belt piece
120$b$, 121$b$ . . . Back surface of second belt pieces 120 and 121

The invention claimed is:

1. A pair of belt-attached pants comprising:
a pants main body having a waistband part in a tubular shape provided at an upper end part of the pants main body, and having a waist part that is a tubular part configured to cover a lower abdomen above a pubis of a human body and below the waistband part when worn, at least the waist part having stretchability;

a first belt having a first fixed part that is fixed to a back surface of the waist part, the first belt having two first other parts sandwiching the first fixed part, the first other parts going around from a back surface side to a front surface side along the waist part while facing each other, the first other parts being fixed to a front surface of the waist part at a predetermined interval;

a second belt having a second fixed part that is fixed to the front surface of the waist part, the second belt having two second other parts sandwiching the second fixed part, the second belt having a length in which the two second other parts reach at least both side parts of the waist part respectively to sides away from the second fixed part on the front surface along the waist part while facing each other; and a fastening part that makes one of the second other parts fastenable to one of the first other parts and makes the other of the second other parts fastenable to the other of the first other parts, wherein the first belt and the second belt are formed of a member having stretchability lower than stretchability of the waist part, and the second belt is configured to support the lower abdomen above the pubis of the wearer upward by fastening the first other parts to the second other parts through the fastening part.

2. The pair of belt-attached pants according to claim 1, wherein the second fixed part of the second belt is located in a center of the second belt in a longitudinal direction of the second belt wherein the second fixed part is disposed in a center of the front surface of the waist part, the first fixed part of the first belt is located in a center of the first belt in a longitudinal direction of the first belt wherein the first fixed part is disposed in a center of the back side of the pants main body.

3. The pair of belt-attached pants according to claim 1, wherein the fastening part is composed with two of fastening members wherein the fastening members are disposed at left and right sides of the pair of belt-attached pants, one of the fastening members at the right side is configured to fasten the one of the first other parts at the right side to the one of the second other parts at the right side, the other of the fastening members at the left side is configured to fasten the other of the first other parts at the left side to the other of the second other parts at the left side.

4. The pair of belt-attached pants according to claim 1, wherein in the first belt, a portion at which the one of the first other parts is fixed to the front surface of the waist part is defined as a front fixed portion, in the one of the first other parts, a non-fixed part is determined between the front fixed portion and the first fixed part, and is not fixed to the waist part, and the non-fixed part has a length greater than a partial length of the waist part that corresponds to the non-fixed part and that is determined between the front fixed portion and the first fixed part under a condition where the waist part is not stretched such that a gap is created between the non-fixed part and the waist part.

5. The pair of belt-attached pants according to claim 4, wherein in the other of the first other parts, another front fixed portion is defined by the same rule as for the one of the first other parts, and another non-fixed part is determined from the another front fixed portion and the first fixed part, and the another non-fixed part also has a length greater than a partial length of the waist part that corresponds to the another non-fixed part and that is determined between the another front fixed portion and the first fixed part under the condition where the waist part is not stretched such that another gap is created between the another non-fixed part and the waist part.

* * * * *